United States Patent
St. Onge et al.

(10) Patent No.: US 6,605,088 B1
(45) Date of Patent: Aug. 12, 2003

(54) BONE SETTING APPARATUS AND METHOD

(76) Inventors: Richard A. St. Onge, 4151 S., 600 East, Millville, UT (US) 84326; Gordon Baker, 2685 S., 600 West, Nibley, UT (US) 84321; T. Wade Fallin, 210 E., 200 South, Hyde Park, UT (US) 84318

( * ) Notice: Subject to any disclaimer, the term of this patent is extended or adjusted under 35 U.S.C. 154(b) by 0 days.

(21) Appl. No.: 09/526,662

(22) Filed: Mar. 15, 2000

(51) Int. Cl.$^7$ ............................................. A61B 17/64
(52) U.S. Cl. ........................................ 606/54; 606/57
(58) Field of Search .......................... 606/54, 57, 105

(56) References Cited

U.S. PATENT DOCUMENTS

| | | | | |
|---|---|---|---|---|
| 4,365,624 A | * | 12/1982 | Jaquet | 606/57 |
| 4,483,334 A | * | 11/1984 | Murray | 606/54 |
| 4,628,922 A | * | 12/1986 | Dewar | 606/54 |
| 4,988,349 A | * | 1/1991 | Pennig | 606/57 |
| 5,207,676 A | * | 5/1993 | Canadell et al. | 606/57 |
| 5,578,032 A | | 11/1996 | Lalonde | |
| 5,624,440 A | * | 4/1997 | Huebner | 606/54 |
| 5,746,741 A | * | 5/1998 | Kraus et al. | 606/54 |
| 5,769,851 A | * | 6/1998 | Veith | 606/54 |
| 5,797,919 A | | 8/1998 | Brinson | |
| 5,827,282 A | * | 10/1998 | Pennig | 606/54 |
| 6,030,387 A | * | 2/2000 | Ballier | 606/54 |

* cited by examiner

*Primary Examiner*—Paul J. Hirsch
(74) *Attorney, Agent, or Firm*—Pandiscio & Pandiscio

(57) ABSTRACT

A pair of bone clamps used for open reduction and internal fixation of a fractured bone or osteotomy is interconnected by a lockable, articulating connection apparatus. Each bone clamp includes a primary clamping means for manipulating a bone fragment back into a proper position. Additionally, each bone clamp includes a secondary bone clamping means that provides adequate clamping force for maintaining the reduction so that the primary clamping means can be released. The secondary bone clamping means provides clearance for the positioning and application of a fracture fixation prosthesis to stabilize the reduction during healing. The bone clamps and lockable, articulating connection apparatus together comprise a bone setting apparatus that provides for unconstrained manual reduction and alignment of the bone fracture, locking of the reduction in a fixed position and orientation, and application of a fracture fixation prosthesis, thereby securing the reduction.

17 Claims, 18 Drawing Sheets

BONE SETTING APPARATUS AND METHOD

BACKGROUND OF THE INVENTION

1. Field of the Invention

The present invention relates generally to surgical bone clamps and more specifically to devices used to hold and manipulate bone fragments in order to reduce a fracture or osteotomy.

2. Description of Related Art

There are commercially available a number of bone clamping devices that facilitate the open reduction of a bone fracture or osteotomy. Most commonly, these clamps contact the subject bone at the surface directly exposed at the surgical incision and at the corresponding surface on the far side of the bone. After successful repositioning of the bone fragments so that they are in proper alignment, the bone clamps must be removed to provide access for a fixation device, most commonly a bone plate and bone screws. Before applying the bone plate, a malleable template is first placed at the repair site and bent to conform to the bony anatomy. Next, the bone plate is bent to match the shape of the formed template, and then the bent bone plate is applied to the surgical site. If the templating or subsequent forming of the bone plate is not precise, the procedure must be repeated. Once the bone plate adequately conforms to the bone anatomy, it is used to secure the fracture or osteotomy. The bone plate bridges the defect and typically provides a number of apertures to receive bone screws that secure the plate to the bone.

Upon release of the bone clamps to provide clearance for the malleable template or the bone plate, the reduction is left unsecured and frequently shifts due to soft tissue tension or structural compromise due to bone defects at the fracture site. This necessitates the reapplication of the bone clamps and realignment of the bone fragments. Given the trial and error nature of forming the malleable template and bending the bone plate, this sequence may need to be repeated several times before the bone plate is successfully applied so that the bone fragments are secured in proper alignment. Each repeated sequence increases operating room time, increasing blood loss, increasing anesthesia time and thereby increasing risk to the patient of anesthesia complications, and increasing potential iatragenic tissue damage.

Accordingly, attempts have been made to improve upon this challenging and sometimes frustrating surgical procedure. U.S. Pat. No. 5,797,919 to Brinson provides for a bone clamp that holds the bone fragment by clamping diametrically opposed surfaces. The line of clamping is orthogonal to the plane of surgical access, leaving the bone surface at the incision accessible for a template or bone plate. However, because the clamping surfaces approach the bone surface from the sides, a wider incision is required and more soft tissue is displaced and potentially damaged. Additionally, when two such bone clamps are required to urge two bone fragments back into proper alignment, the clamps must be held manually while the template and bone plate are applied. The member of the surgical team holding the bone clamps may become fatigued during the lengthy trial and error stage of bone plate templating, thereby compromising the accuracy of the reduction.

Another attempt to improve on the surgical efficiency of fracture reduction is found in U.S. Pat. No. 5,578,032 to Lalonde. This patent describes a bone clamp with a ratchet locking scissors mechanism that actuates clamping surfaces. The clamping surfaces contact the bone at the incision site on the near and far sides of the bone, thereby minimizing the exposure required. It further describes a connection bar that locks two clamps into a fixed relative position. This apparatus has several disadvantages. First, the scissors mechanism requires all of the manipulation force to be transmitted through a thumb and finger. This greatly limits the amount of distraction and repositioning force that can be applied to the bone fragments. Secondly, the connecting bar, when unlocked so that the bone clamps are movably connected to the connecting bar, only permit translation along a single axis. This motion would only accommodate fractures that are displaced along a single axis and require no rotational or orthogonal translation correction. Such a fracture rarely occurs in practice. Finally, the bone is clamped between two sharp points, which are only adequate for manipulating very small bones, such as the metacarpals and phalanges. Larger contact surfaces are required to forcefully manipulate larger bones.

It would therefore be an improvement in the medical arts to provide a bone setting apparatus that facilitates the rigid holding of a fracture reduction while concurrently providing access for templating and application of a fracture fixation prosthesis, such as a bone plate or intramedullary rod.

SUMMARY OF THE INVENTION

It is an object of the invention to provide a bone setting apparatus that allows for unconstrained repositioning and realignment of the bone fragments.

It is a further object of the invention to provide a bone setting apparatus that can be locked to hold a fixed position and alignment between bone fragments.

It is yet a further object of the invention to provide a bone setting apparatus that provides adequate mechanical advantage for manipulating and reducing a fracture.

It is still a further object of the invention to provide a bone setting apparatus that provides clear access for a fracture fixation prosthesis and associated templates thereof.

It is still another object of the invention to provide a temporary clamp to hold a bone plate in position while it is secured to the bone with screws.

It is yet a further object of the invention to increase the efficiency of the surgical procedure for reducing a bone fracture and applying a fracture fixation prosthesis and thereby decrease blood loss, anesthesia time, risk of infection, and iatragenic tissue damage.

In the preferred embodiment, a bone setting apparatus is comprised of two bone clamps and a lockable, articulating connection apparatus. Each bone clamp includes a primary clamping means for manipulating a bone fragment back into a proper position. Additionally, each bone clamp includes a secondary bone clamping means that provides adequate clamping force for maintaining the reduction when the primary clamping means is released. Furthermore, the secondary bone clamping means provides clearance for the positioning and application of a fracture fixation prosthesis (e.g., a bone plate) to maintain the reduction during healing. Moreover, once a fracture fixation prosthesis is positioned adjacent to the bone while the fracture is securely held by the secondary clamping means, the primary clamping means can be used to hold the fracture fixation prosthesis in position while it is secured to the bone by bone screws or the like.

The combination of two bone clamping means provides a unique advantage. The primary bone clamping means has greater surface contact with the bone, thereby permitting greater forces to be applied to manipulate the bone fragments into proper alignment. Once the reduction is accomplished, lesser forces are required to maintain the bone alignment. Thus, the secondary clamping means requires less bone surface contact, thereby increasing the amount of unobstructed bone surface. This increased accessibility to the exposed bone surface permits adequate access for application of a template and fracture fixation prosthesis.

Another advantage of the bone clamp is an independent clamping actuation mechanism and holding surface. Once the bone clamp is secured to the bone fragment, the user can use a full hand grasp to have maximum leverage for manipulating the bone fragments into proper alignment.

Each bone clamp is attached to a rod by a lockable, articulating joint. The joints can be locked so that a fixed position and orientation are secured between the two bone clamps. In their unlocked state, the joints provide for unconstrained repositioning and reorientation between the bone clamps. The joints and the rod together comprise a connection apparatus for the two bone clamps.

The bone clamps and connection apparatus comprise a bone setting apparatus that facilitate the following surgical technique:

(a) securing each bone clamp to a bone fragment using the primary clamping means;

(b) manual reducing and approximating the bone fracture without any spatial constraint;

(c) locking the reduction in position and orientation with the connection apparatus;

(d) applying the secondary clamping means and releasing the primary clamping means, thereby creating clear access to the exposed bone surface;

(e) positioning a fracture fixation prosthesis at the surgical site;

(f) securing the fracture fixation prosthesis by the primary bone clamping means;

(g) securing the fracture fixation prosthesis to the bone by bone screws or the like; and (h) removing the bone clamps.

In a further embodiment, each bone clamp has only a single bone clamping means. The counter opposed surfaces of the bone clamping means define a plane of clamping that is at an acute angle to the plane of the surgical incision. The acute angle is large enough so that the exposed bone surface is unobstructed for application of a fracture fixation prosthesis. While this apparatus may require a larger incision, it will eliminate the procedural step, in the preferred embodiment described above, of securing a secondary clamping means and releasing a primary clamping means. This increase in surgical efficiency can outweigh the tradeoffs with a larger incision.

In yet another embodiment, the connection apparatus is attached to each bone clamp by a lockable ball and socket joint. A rod extends from each joint. One rod is solid, and the other rod is tubular with a locking means, such as a thumb screw. The solid rod telescopes, or pistons, within the tubular rod, allowing a sliding motion therebetween. This combination of two ball and socket joints and a piston joint permit unconstrained spatial positioning, both translational and rotational, when the joints are unlocked.

It should be appreciated that various combinations of translating and rotating joints may be used to enable unconstrained spatial positioning for two objects attached to the end of a connection apparatus. In the preferred embodiment, the joints attached to one bone clamp simulate a spherical coordinate system by providing two orthogonal rotation axes and one radial translation. In the alternative embodiment described above, the ball and socket joint combined with the telescoping rod also simulates a spherical coordinate system. Similarly, one could provide three orthogonal translating joints to simulate a Cartesian coordinate system, or one could provide one rotation axis and two orthogonal translation axes to simulate a cylindrical coordinate system.

The above, and other objects, features and advantages of the present invention, will become apparent from the following description read in conjunction with the accompanying drawings.

DETAILED DESCRIPTION OF THE PREFERRED EMBODIMENT

Figure 1:
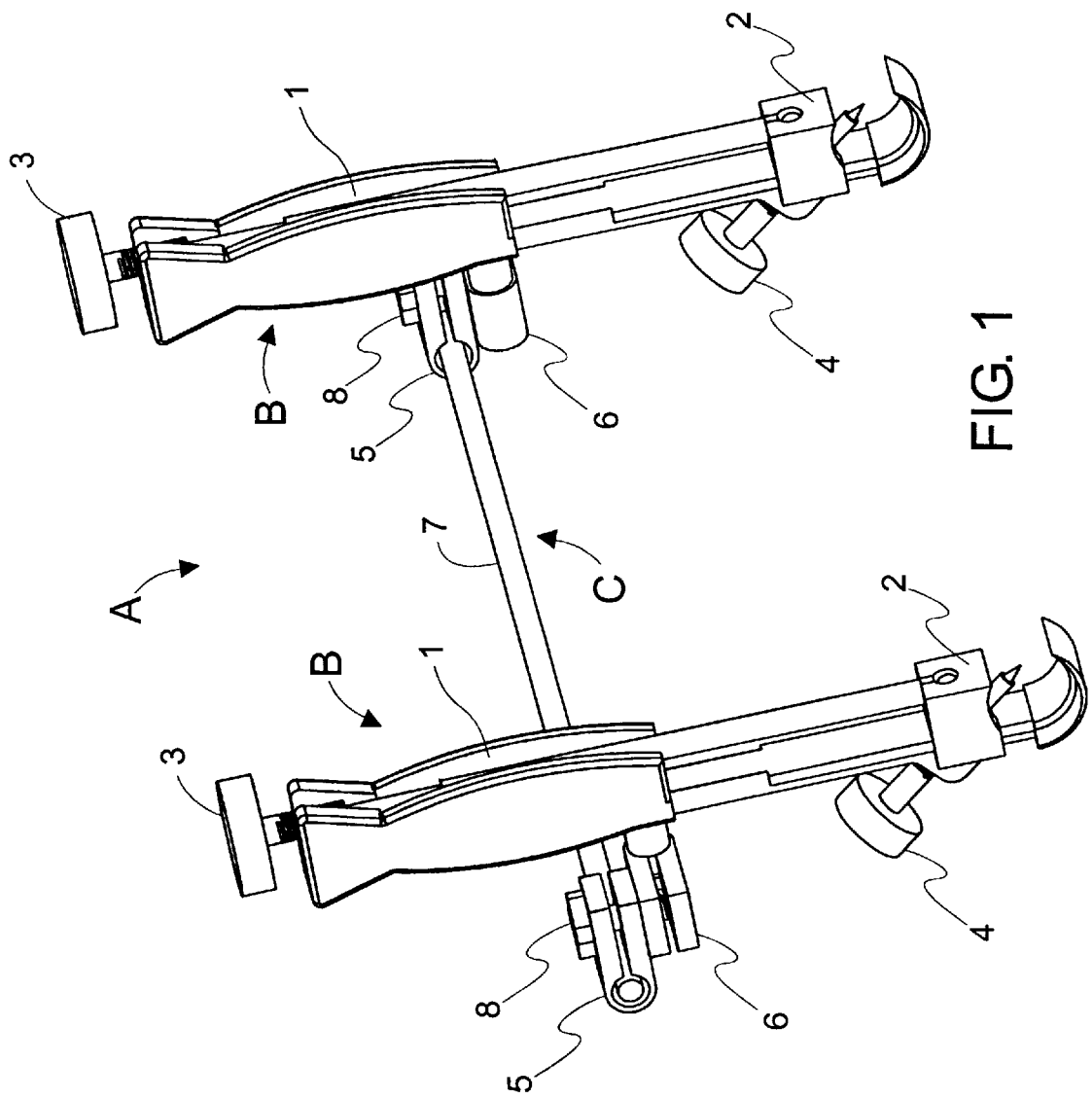
FIG. 1 is a perspective view of novel bone setting apparatus formed in accordance with the present invention.

Referring now to FIG. 1, there is shown a bone setting apparatus A formed in accordance with the present invention. Bone setting apparatus A is comprised of two handles 1, two top clamps 2, two primary clamp shafts 3, two secondary clamp shafts 4, two first joints 5, two second joints 6, connecting rod 7, and two thumbscrews 8. Together, the handle 1, top clamp 2, primary clamp shaft 3, and secondary clamp shaft 4 comprise a bone clamp B. Together, the first joints 5, second joints 6, connecting rod 7, and thumbscrews 8 comprise a connection apparatus C. Together, the two bone clamps B and the connection apparatus C comprise the bone setting apparatus A.

The connection apparatus C is placed in a locked state by tightening the two thumbscrews 8. This prevents any relative translation or rotation between the two bone clamps B. In its unlocked state, the bone clamps B can be freely positioned in three dimensional space within the limits of the length of the connecting rod 7. While the connecting rod 7 can slide in both first joints 5, it could be fixed to one of the first joints 5 and still enable full spatial positioning when the connection apparatus C is in an unlocked state.

Figure 2:
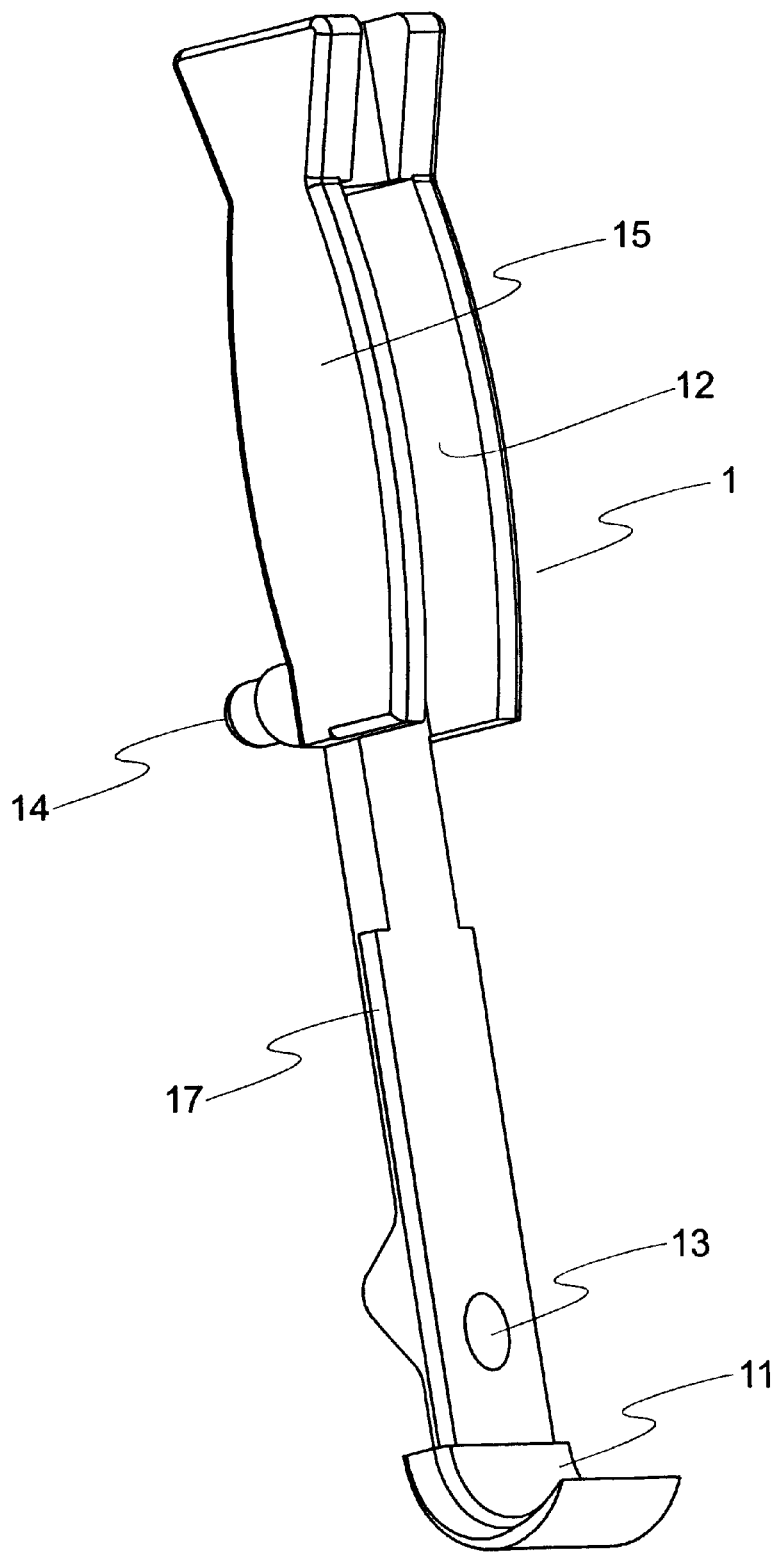
FIG. 2 is a perspective view of the handle component of the bone setting apparatus shown in FIG. 1.

FIG. 2 illustrates the handle 1. It has a lower clamp surface 11 that engages the bone fragment. It also has a slot 12 for receiving the primary clamp shaft 3. Threaded hole 13 is a receptacle for secondary clamp shaft 4. Grip surface 15 allows a full handed grip by the user. Rails 17 articulate with the top clamp 2. Post 14 articulates with second joint 6.

Figure 3:
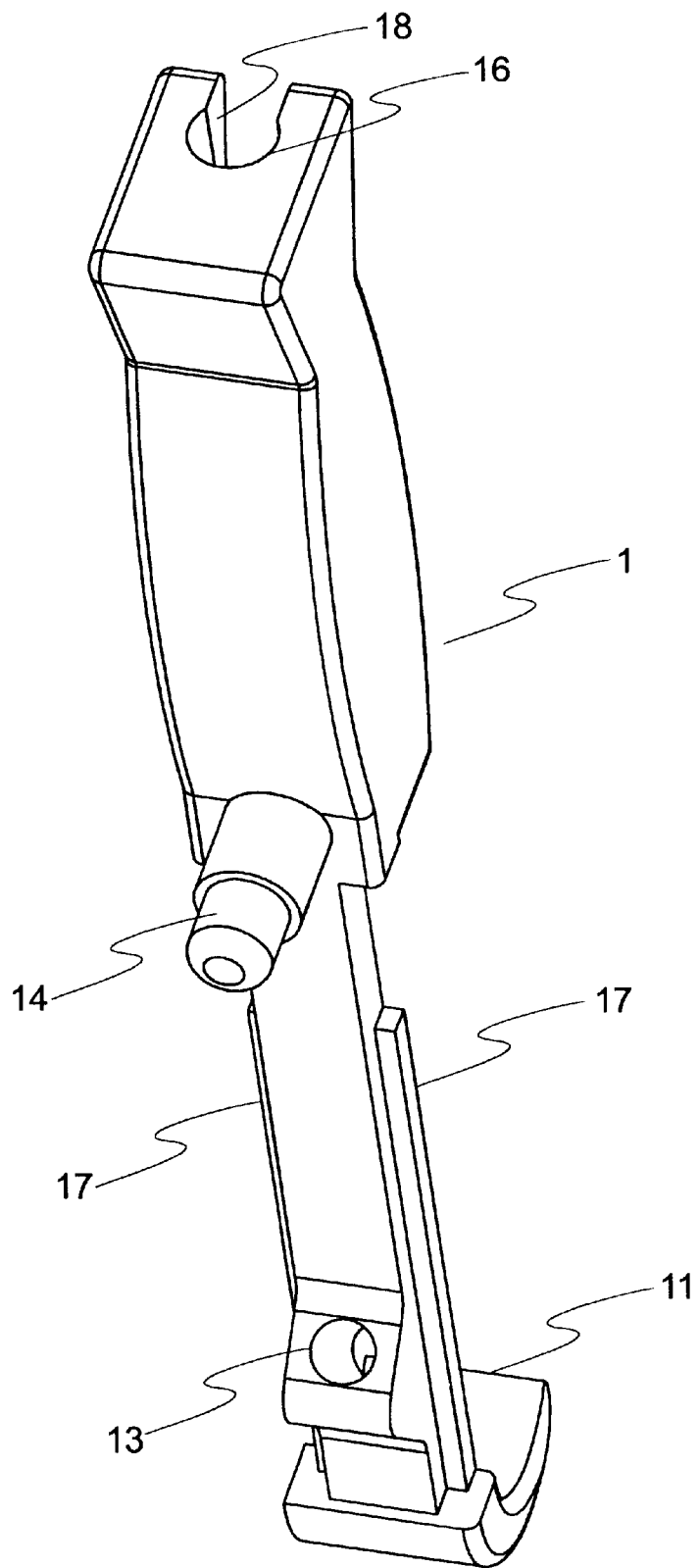
FIG. 3 is another perspective view of the handle component of the bone setting apparatus shown in FIG. 1.

FIG. 3 further illustrates the handle 1. Threaded hole 16 receives the primary clamp shaft 3 to allow the primary clamp shaft 3 to advance the top clamp 2. Threaded hole 16 has a slot 18, on the same side as slot 12, to allow lateral ingress and egress of primary clamp shaft 3 into handle 1.

Figure 4:
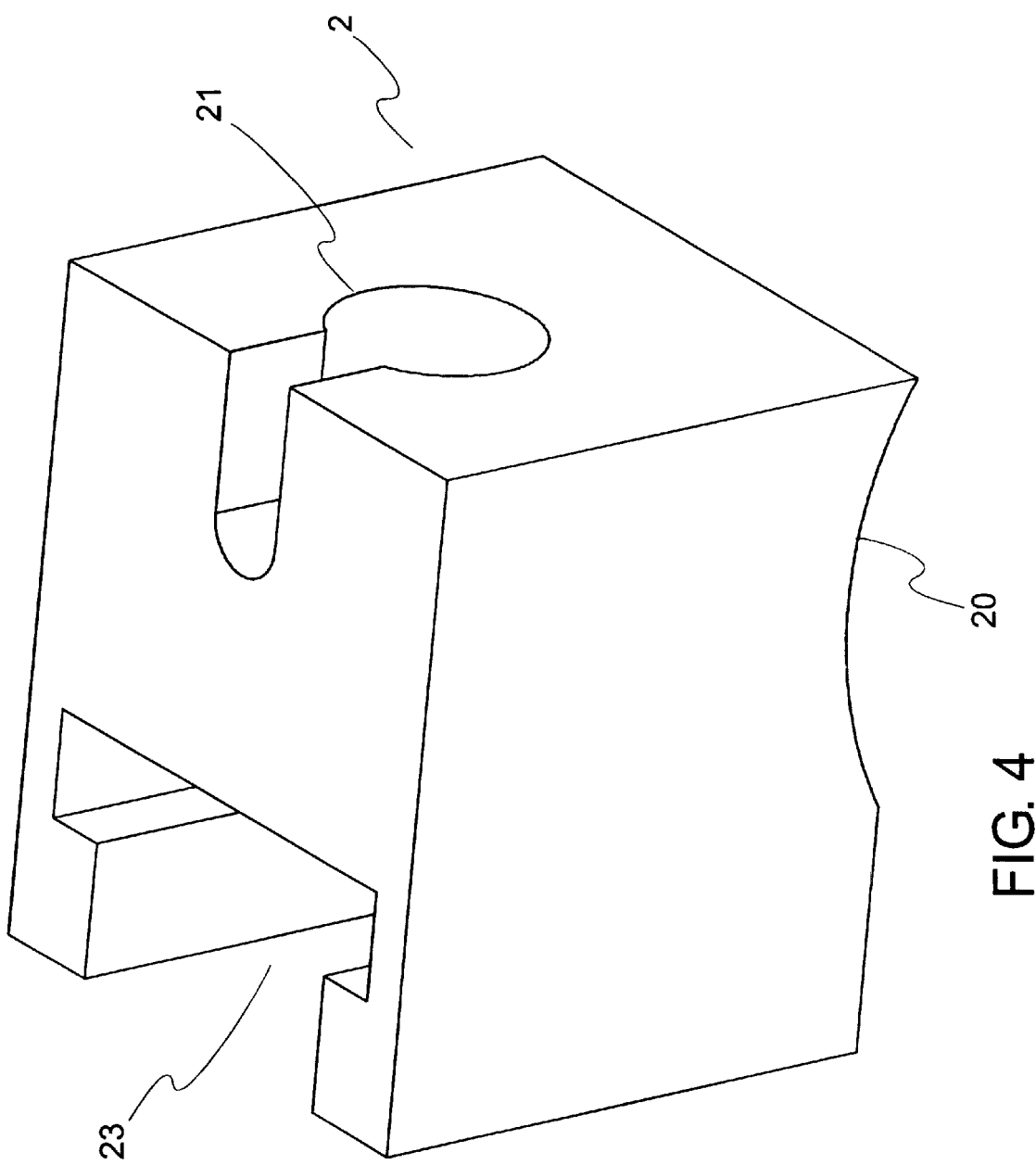
FIG. 4 is a perspective view of the top clamp component of the primary clamping means of the bone setting apparatus shown in FIG. 1.

FIG. 4 illustrates the top clamp 2. T-slot 23 articulates with rails 17 to facilitate a proximal to distal sliding motion. Top clamp 2 has a keyhole 21. Top clamp 2 has top clamping surface 20 that provides counter clamp force with lower clamp surface 11 (FIG. 2) whereby to provide the aforementioned primary clamping means.

Figure 5:
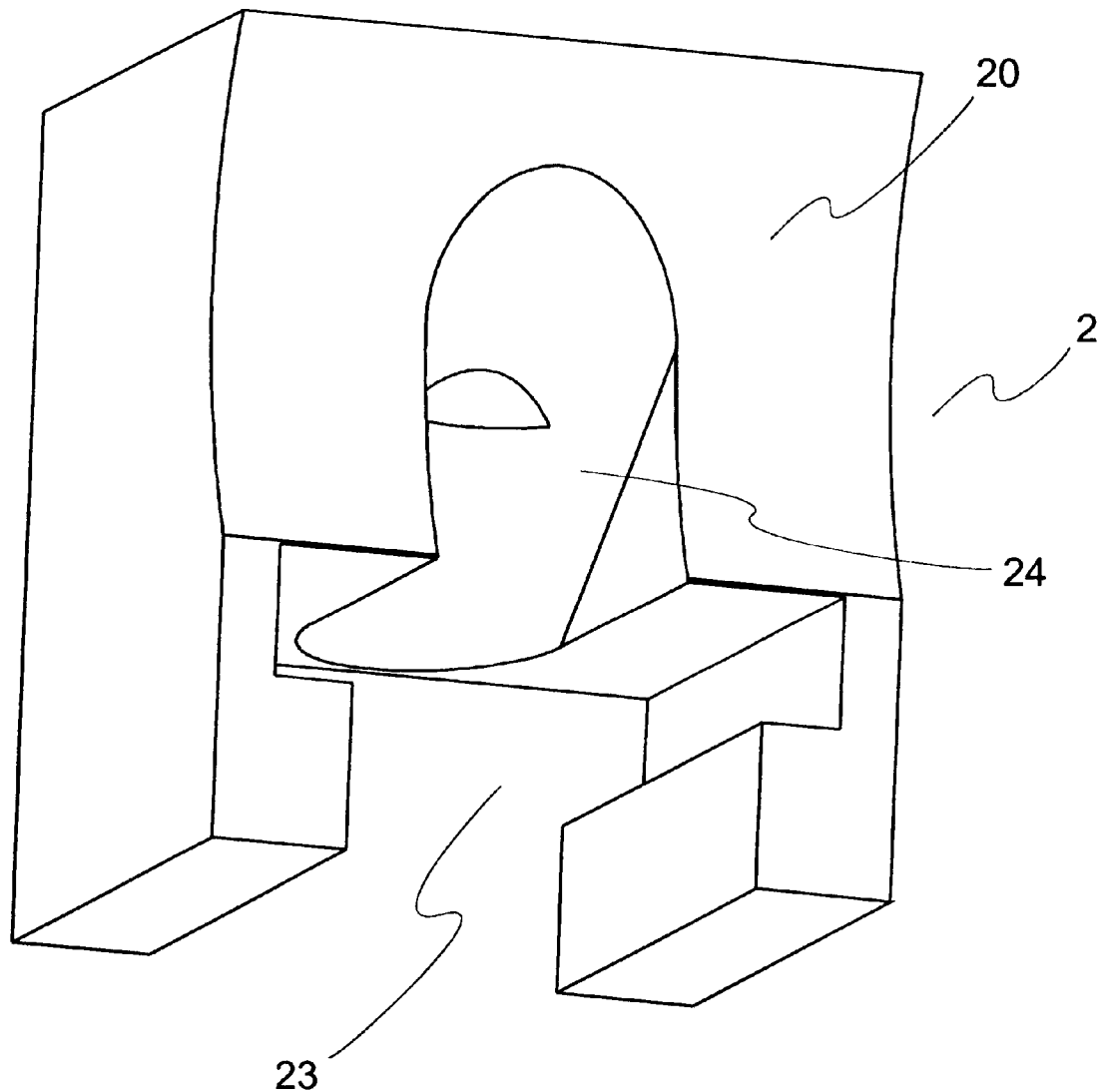
FIG. 5 is another perspective view of the top clamp component of the primary clamping means of the bone setting apparatus shown in FIG. 1.

FIG. 5 further illustrates the top clamp 2. Top clamp 2 has recess 24 which provides clearance for the secondary clamp shaft 4.

Figure 6:
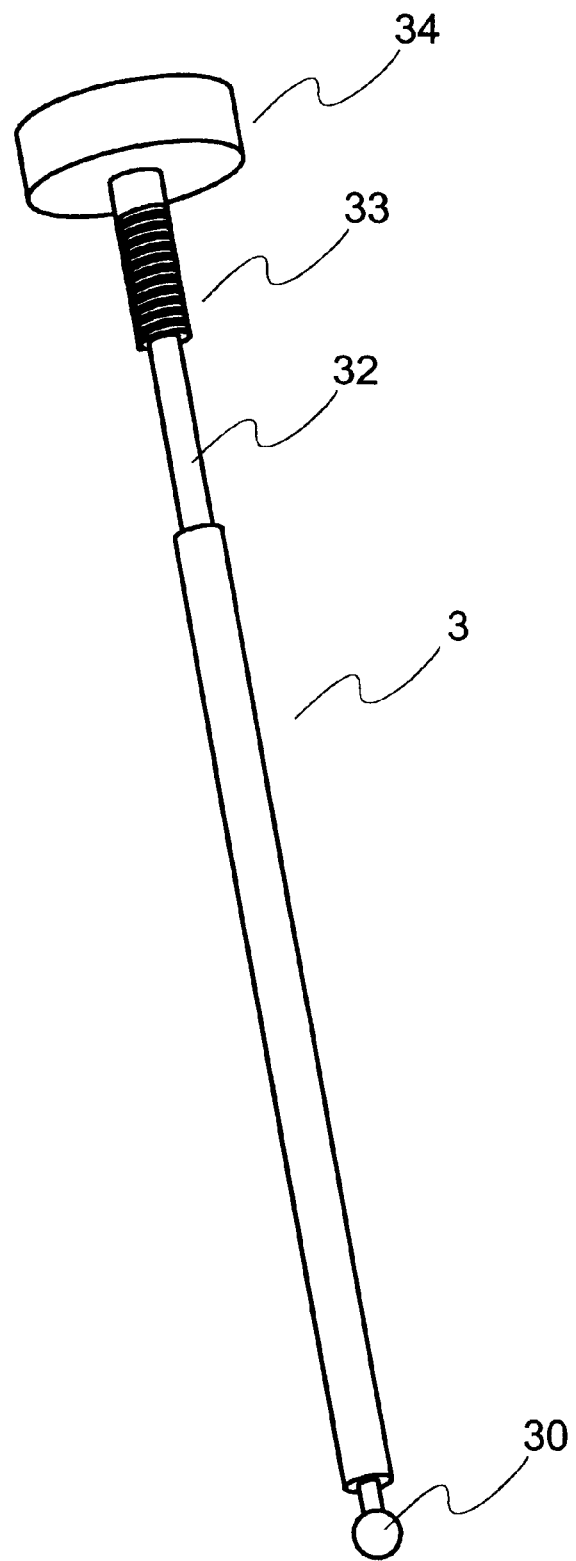
FIG. 6 is a perspective view of the shaft component of the primary clamping means of the bone setting apparatus shown in FIG. 1.

FIG. 6 illustrates the primary clamp shaft 3. Primary clamp shaft 3 has a knob 34 used to turn the shaft. Threads 33 engage threads 16 (FIG. 3) in handle 1. Reduced shaft portion 32 is sized to slide through the slot 18 of threads 16 to facilitate lateral ingress and egress of primary clamp shaft 3 relative to handle 1. Ball tip 30 fits into keyhole 21 in top clamp 2 to transmit motion and clamp force from handle 1 through primary clamp shaft 3 to top clamp 2.

Figure 7:
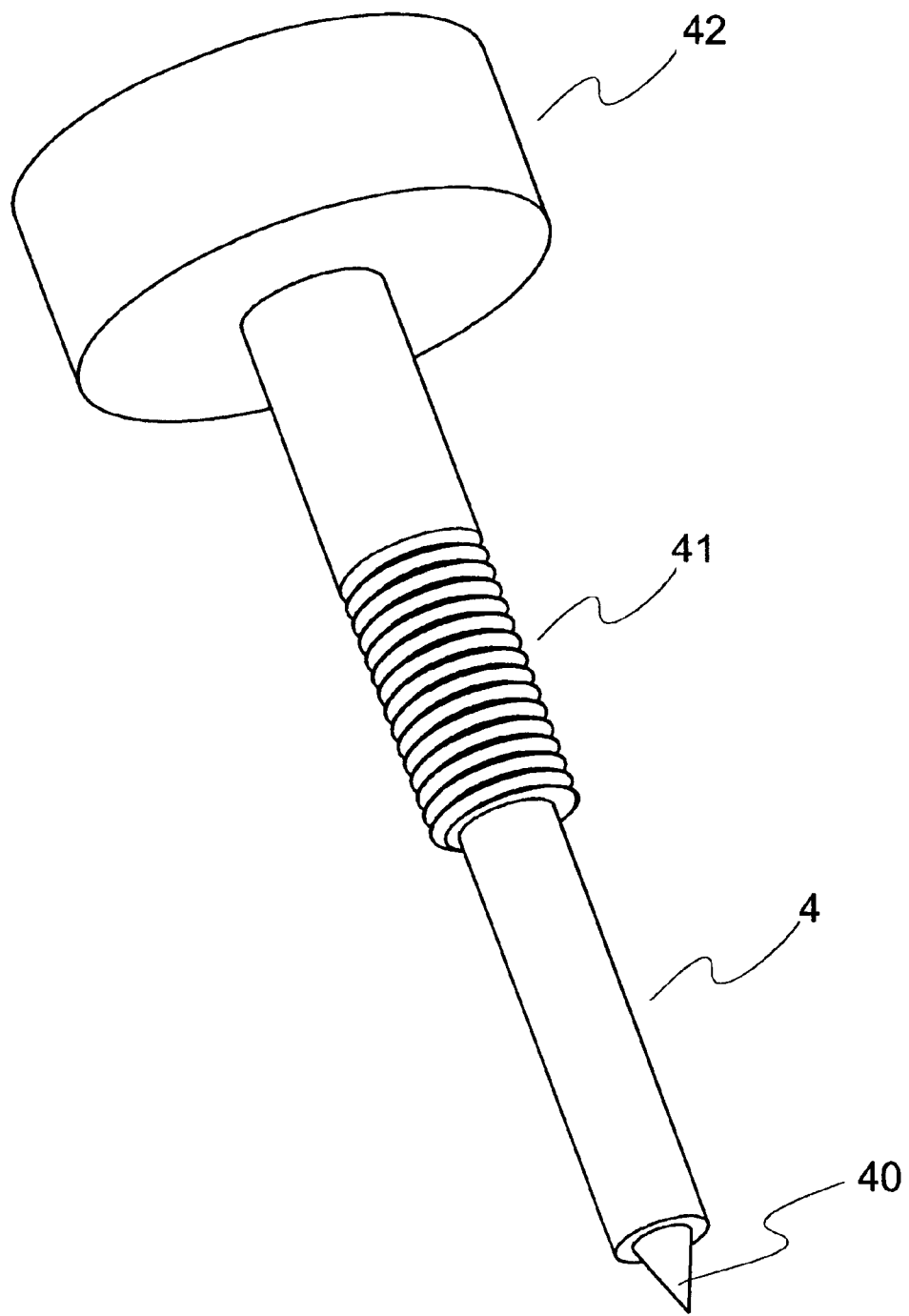
FIG. 7 is a perspective view of the shaft component of the secondary clamping means of the bone setting apparatus shown in FIG. 1.

FIG. 7 illustrates the secondary clamp shaft 4. Secondary clamp shaft 4 has a knob 42 used to turn the shaft. Threads 41 engage threads 13 in handle 1. Spike tip 40 engages the bone surface to provide counter clamp force with lower clamp surface 11 (FIG. 2) whereby to provide the aforementioned secondary clamping means.

Figure 8:
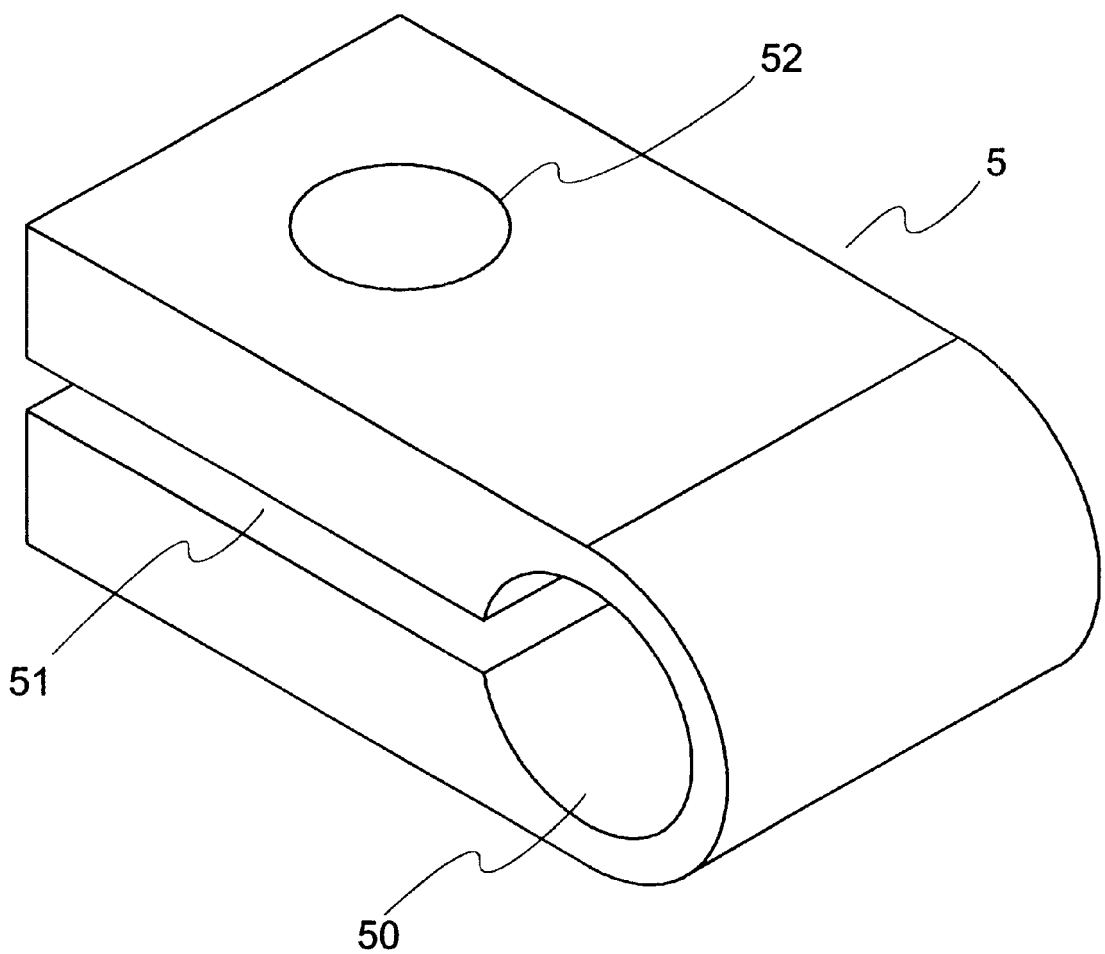
FIG. 8 is a perspective view of the first joint component of the bone setting apparatus shown in FIG. 1.

FIG. 8 illustrates the first joint 5. First joint 5 has a hole 52 which extends all the way through the part. Hole 52 is a clearance hole for thumbscrew 8. Hole 50 articulates with the connecting rod 7. Slot 51 extends from hole 50 to the outside surface of the part.

Figure 9:
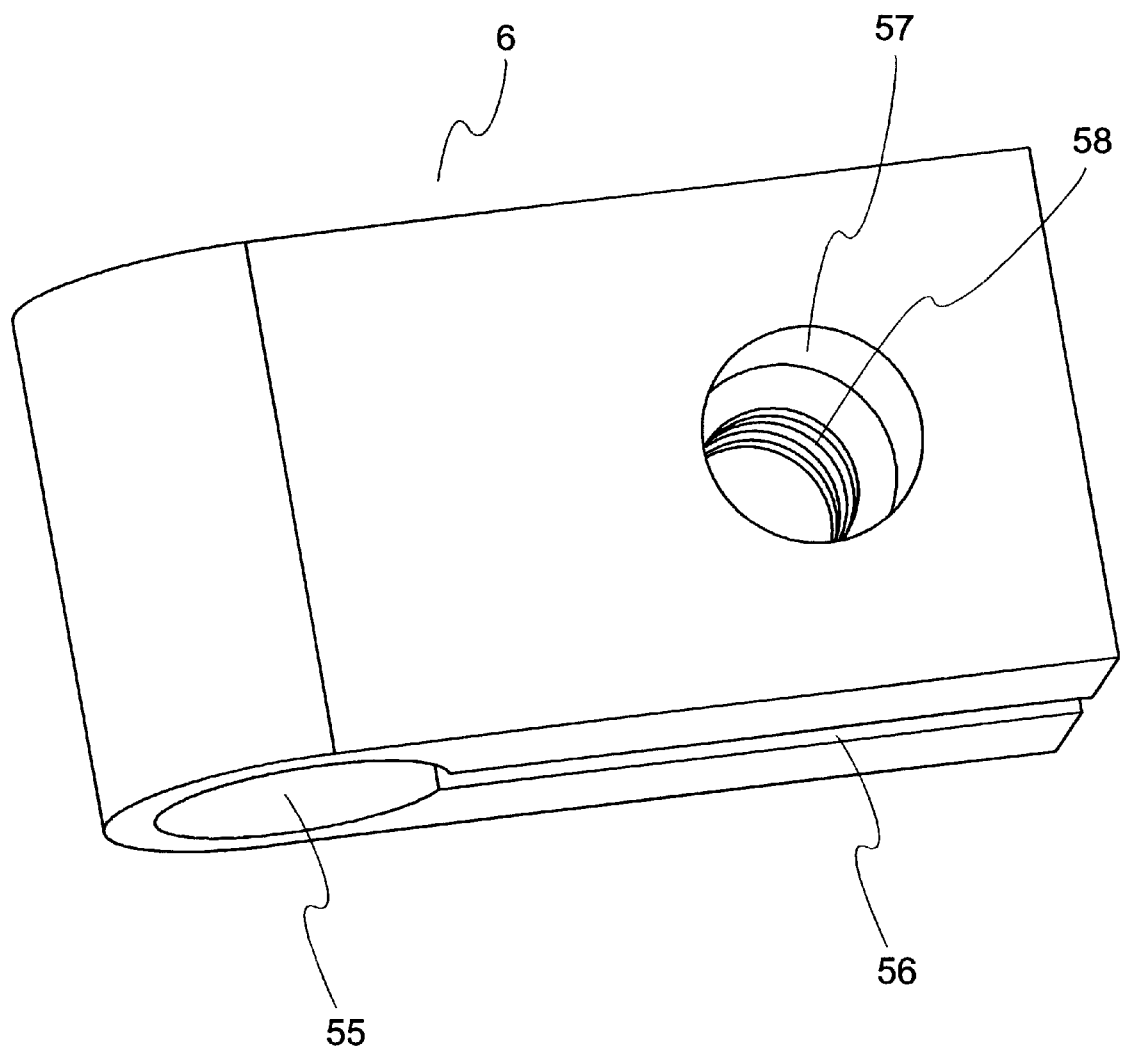
FIG. 9 is a perspective view of the second joint component of the bone setting apparatus shown in FIG. 1.

FIG. 9 illustrates the second joint 6. Second joint 6 has hole 55 which articulates with post 14 (FIG. 2) on handle 1. Slot 56 extends from hole 55 to the outside surface of the part. Hole 57 is a clearance hole for thumbscrew 8. Hole 57 extends from one surface to slot 56. Thread 58 extends from an opposite surface to slot 56.

Figure 10:
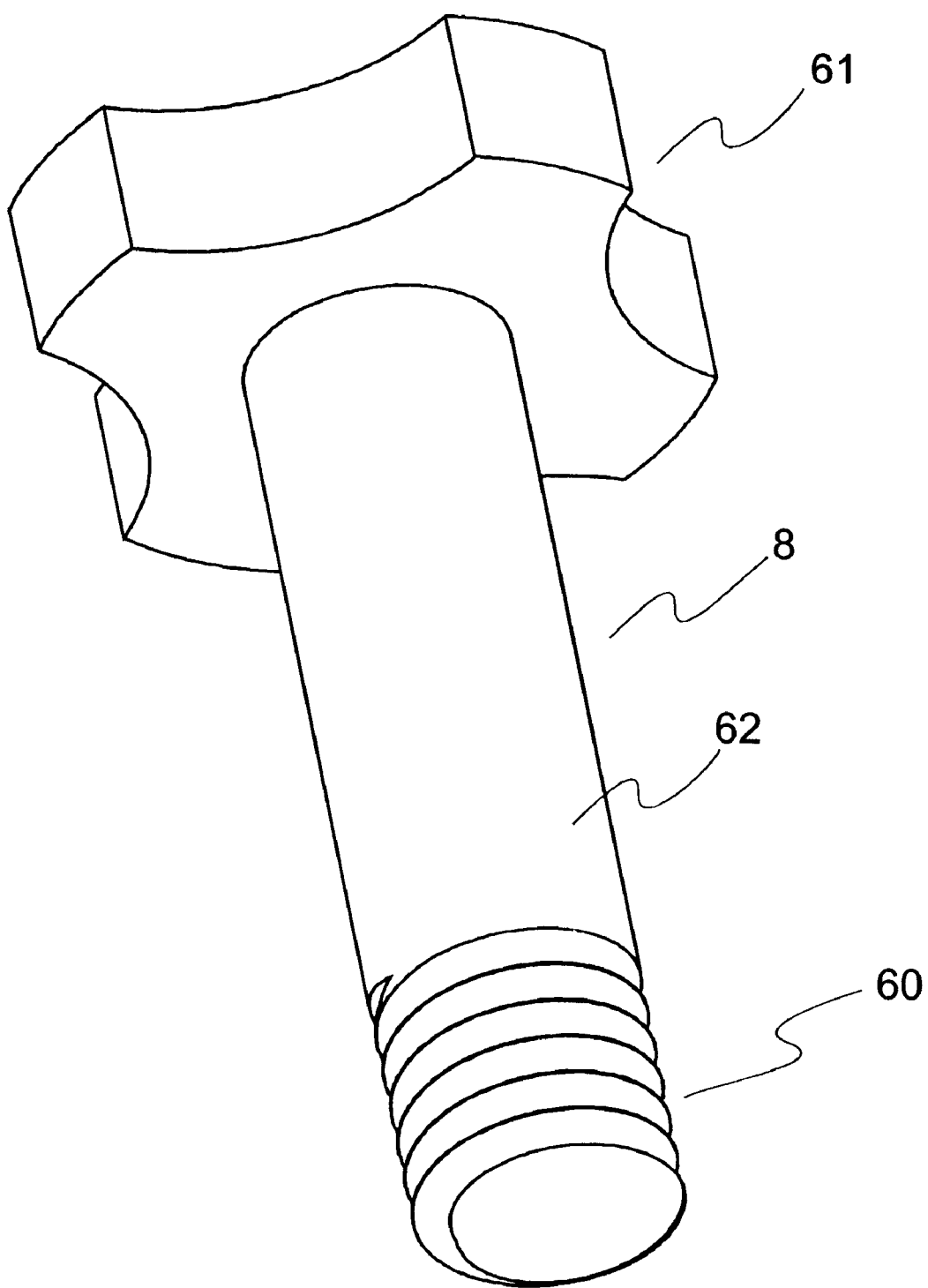
FIG. 10 is a perspective view of the thumb screw component of the bone setting apparatus shown in FIG. 1.

FIG. 10 illustrates the thumbscrew 8. Thumbscrew 8 has a knob 61 for turning and a thread 60 on the end. Thread 60 engages thread 58 (FIG. 9) in second joint 6, and shaft 62 passes through hole 57 in second joint 6 and hole 52 (FIG. 8) in first joint 5. When the thumbscrew 8 is tightened, it causes the slots 51 (FIG. 8) and 56 (FIG. 9) to collapse, thereby clamping the surface of hole 55 (FIG. 9) on post 14 (FIG. 2) and clamping the surface of hole 50 (FIG. 8) on connecting rod 7 (FIG. 1). This clamping action serves to fix the relative position of the two bone clamps B when both thumbscrews 8 are tightened.

Figure 11:
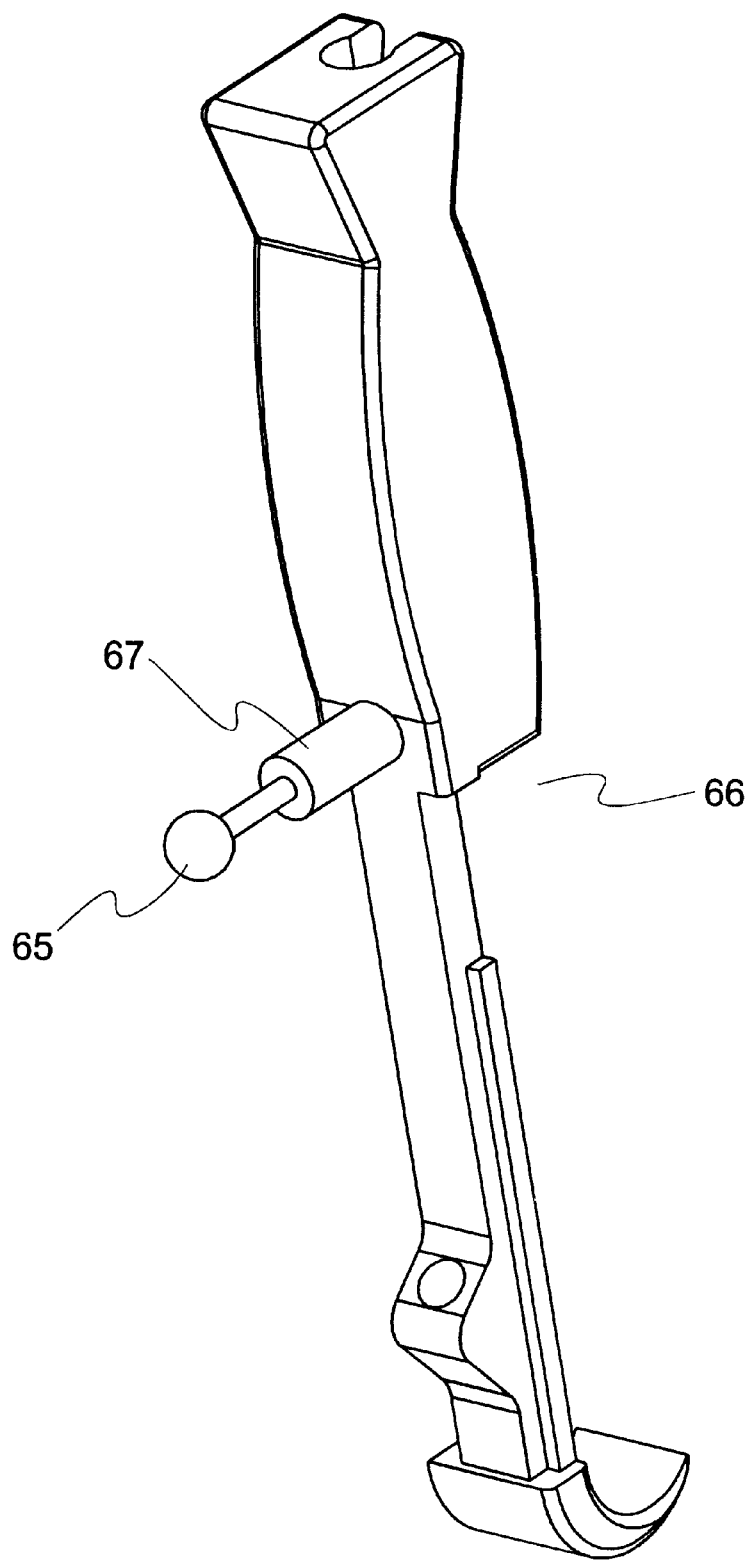
FIG. 11 is a perspective view of an alternative handle component of the bone setting apparatus.

FIG. 11 illustrates an alternative handle 66. Alternative handle 66 has a ball tip 65 on post 67 that articulates with an alternative connection apparatus 70 (see below). Just like handle 1, alternative handle 66 mates with the top clamp 2, primary clamp shaft 3, and secondary clamp shaft 4.

Figure 12:
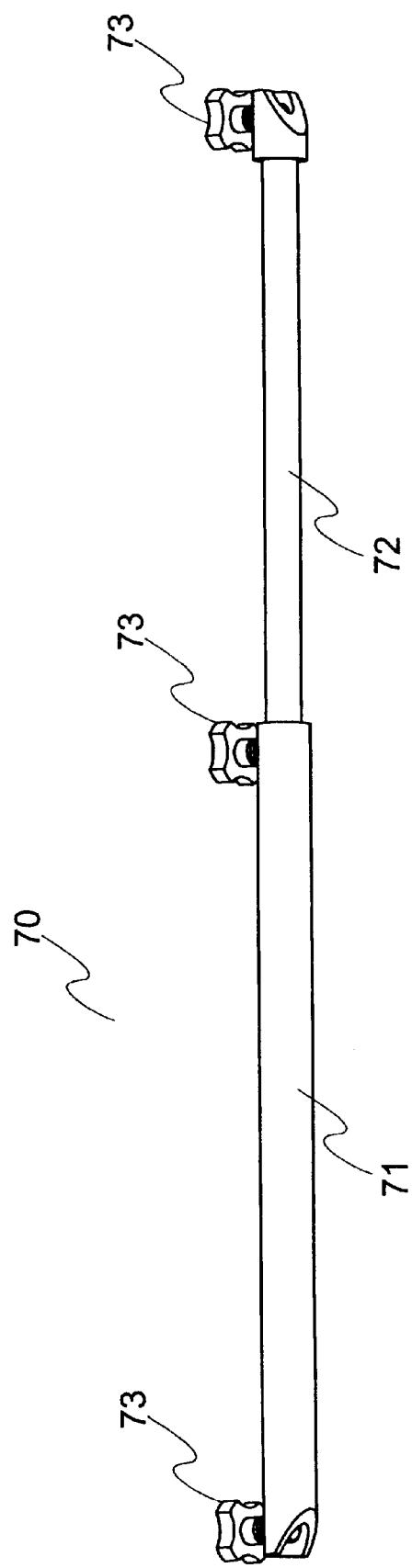
FIG. 12 is a perspective view of an alternative connection apparatus.

FIG. 12 illustrates alternative connection apparatus 70. Alternative connection apparatus 70 is comprised of first connecting rod 71, second connecting rod 72, and three thumbscrews 73.

Figure 13:
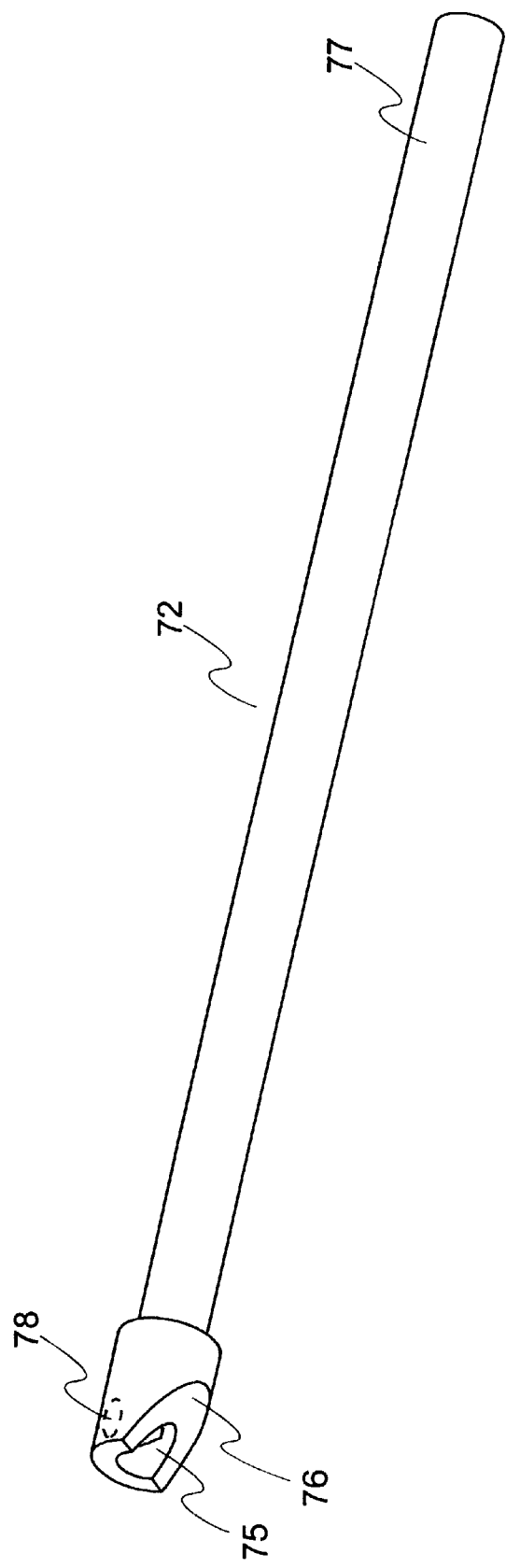
FIG. 13 is a perspective view of the first connecting rod component of the alternative connection apparatus shown in FIG. 12.

FIG. 13 illustrates the second connecting rod 72. Second connecting rod 72 has shaft 77 which is long and solid. It also features a spherical socket 75 which articulates with a ball tip 65 (FIG. 11) on a handle 66. Bevel 76 provides clearance for acute angle positions between the axis of connecting rod 72 and the axis of the post 67 (FIG. 11). Shown in hidden line is threaded hole 78 which engages thumbscrew 73 to lock this second connecting rod 72 to the handle 66.

Figure 14:
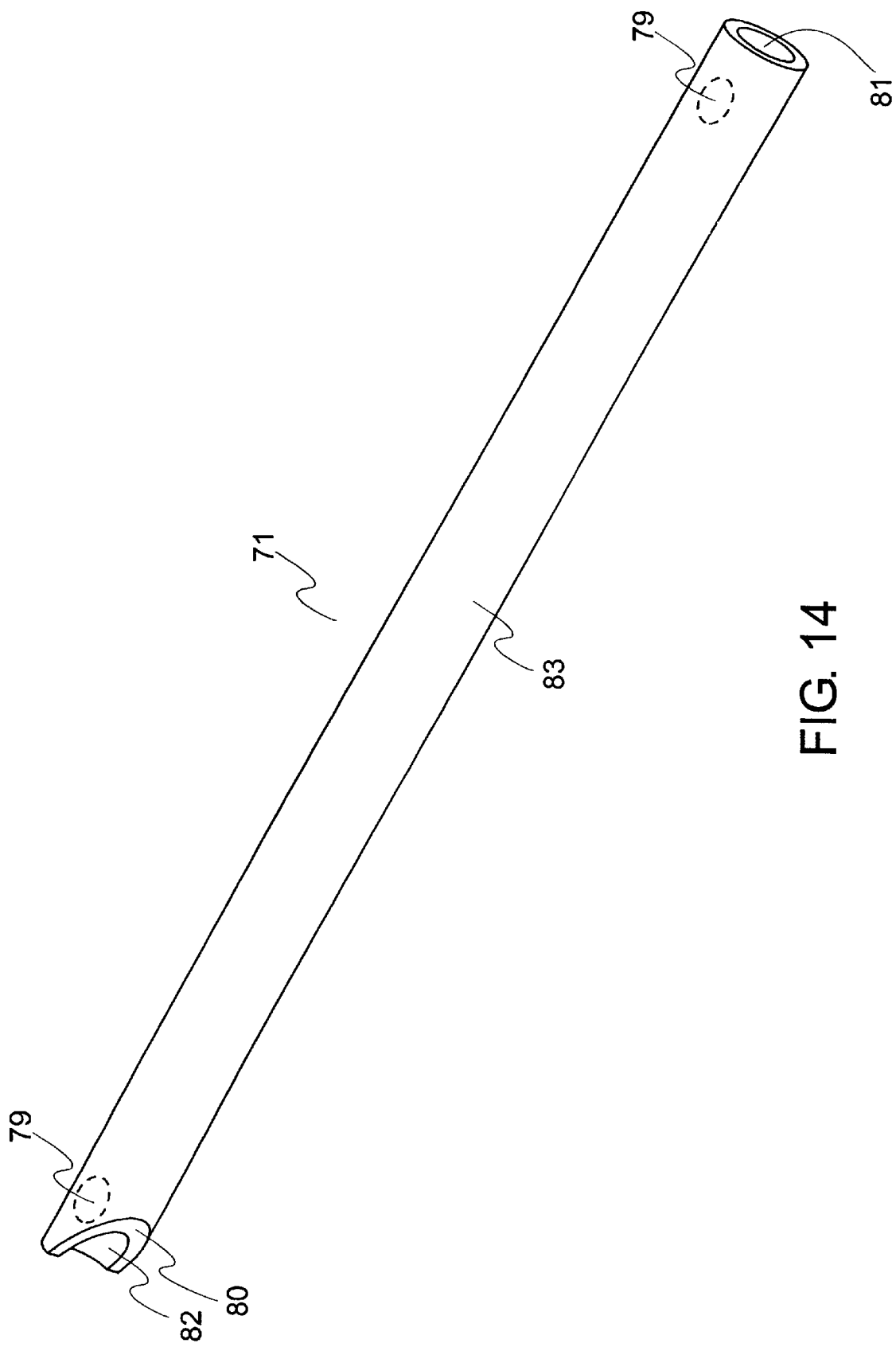
FIG. 14 is a perspective view of the second connecting rod component of the alternative connection apparatus shown in FIG. 12.

FIG. 14 illustrates the first connecting rod 71. First connecting rod 71 has shaft 83 and blind hole 81 which extends most of the length of shaft 83. First connecting rod 71 also features a spherical socket 82 shown in hidden line which articulates with a ball tip 65 (FIG. 11) on a handle 66. Bevel 80 provides clearance for acute angle positions between the axis of connecting rod 71 and the axis of the post 67 (FIG. 11). Threaded holes 79 engage thumbscrew 73 to lock this first connecting rod 71 to the handle 66 on one end, and to lock onto the second connecting rod 72 on the other end.

Figure 15:
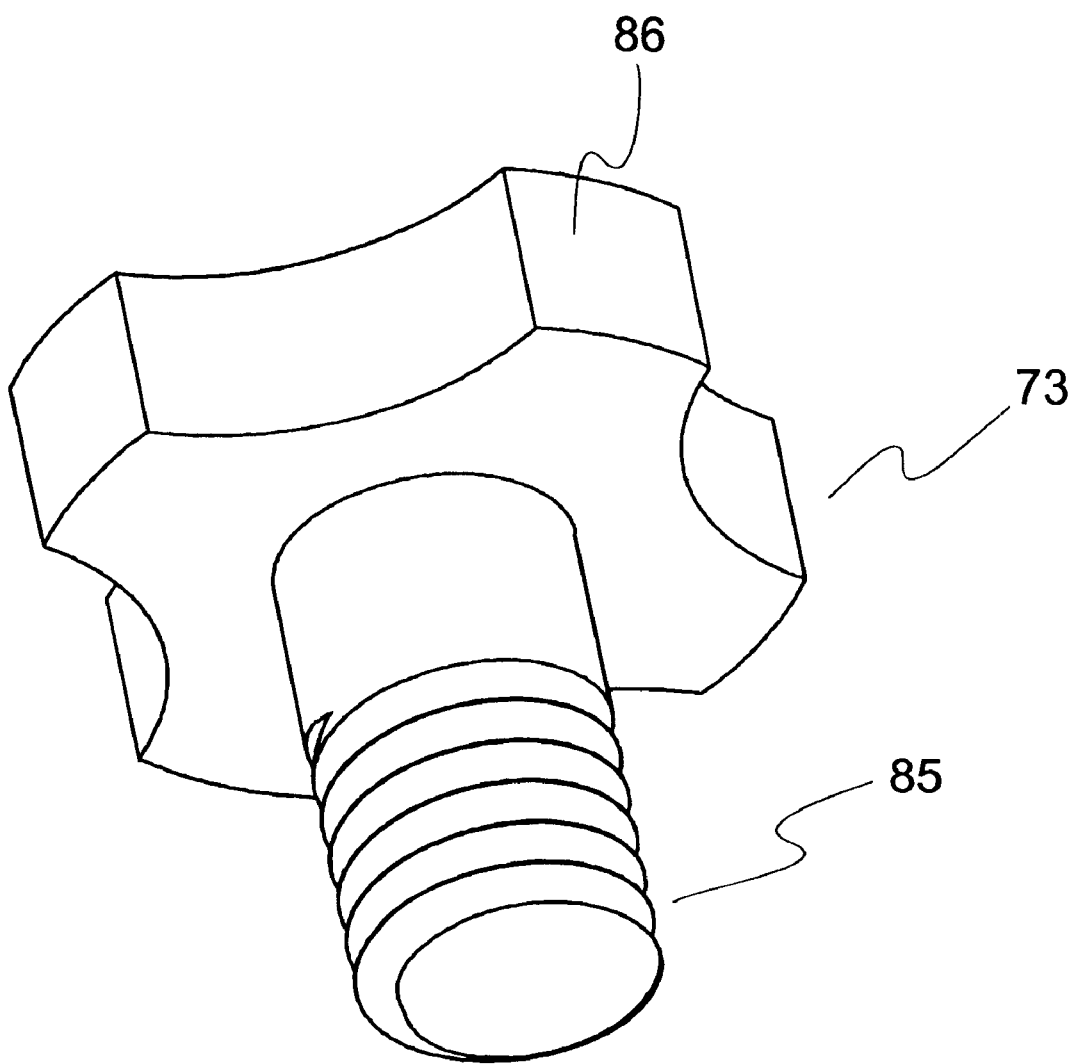
FIG. 15 is a perspective view of the thumbscrew component of the alternative connection apparatus shown in FIG. 12.

The thumb screw 73 is illustrated in FIG. 15. Thumb screw 73 has a knob 86 for turning and threads 85 at the other end.

Figure 16:
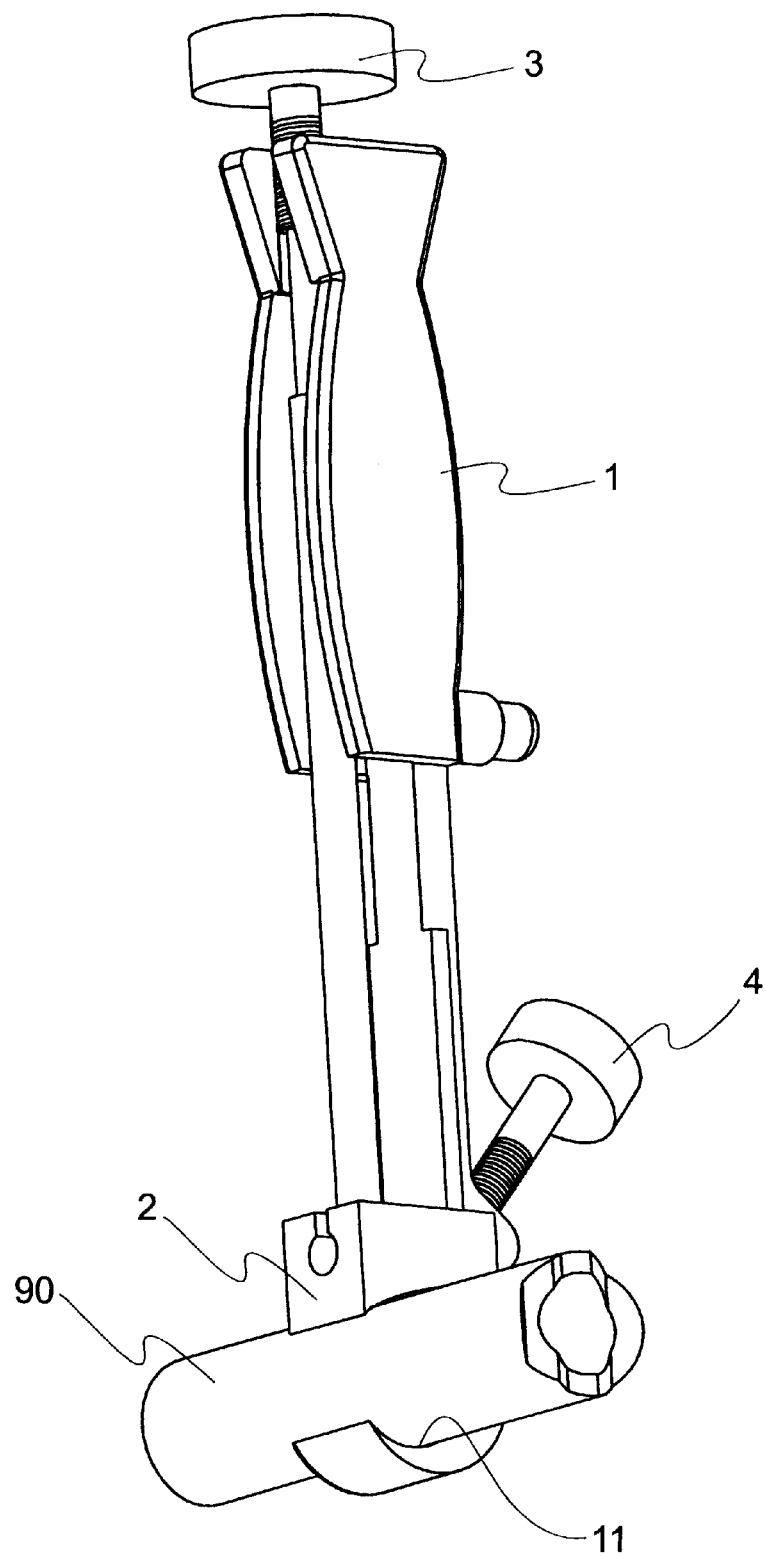
FIG. 16 is a perspective view of the bone clamp holding a bone fragment with the primary clamping means.
Figure 17:
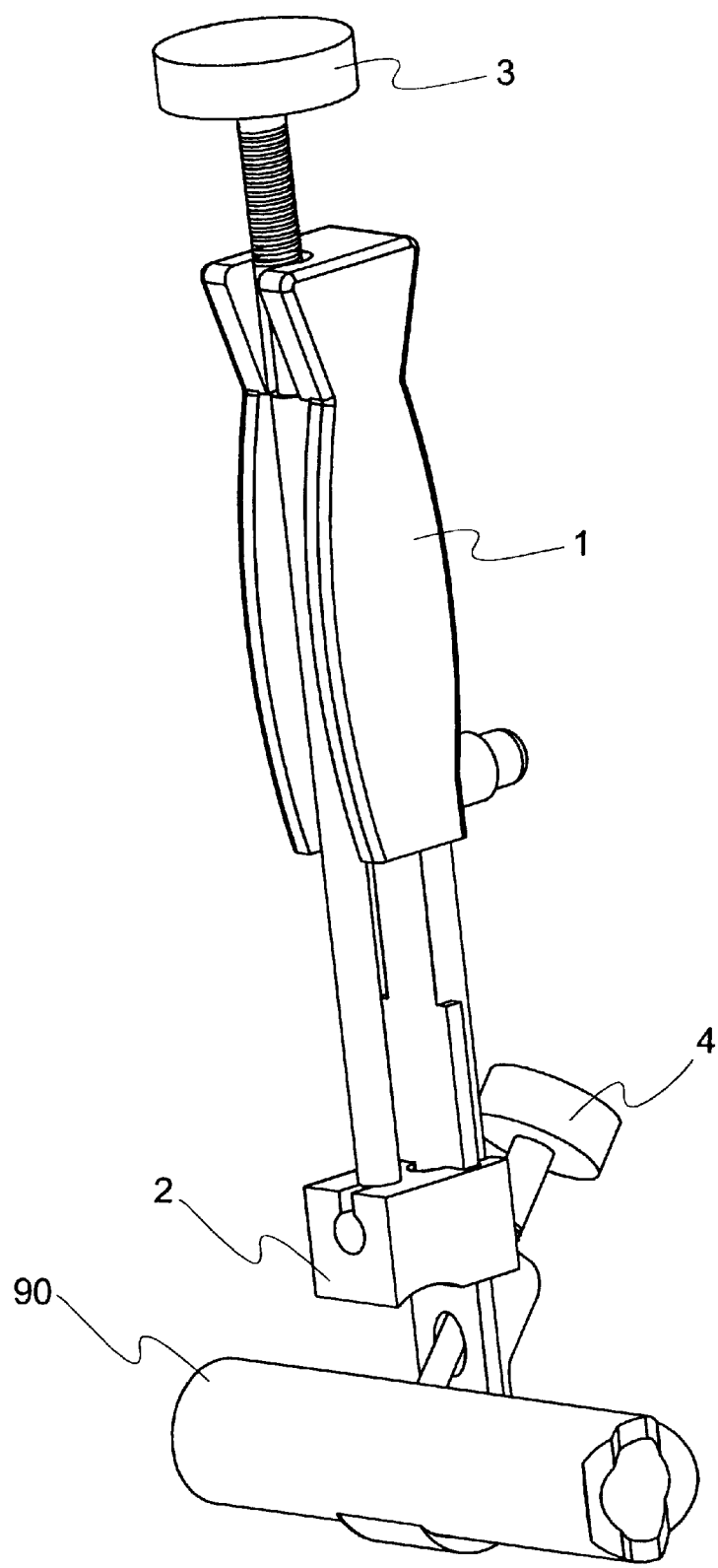
FIG. 17 is a perspective view of the bone clamp holding a bone fragment with the secondary clamping means.

Use of the primary clamping means is illustrated in FIG. 16. The bone fragment 90 is firmly clamped between the top clamp 2 and the bottom clamping surface 11. The clamping force is controlled by the amount of torque delivered to the primary clamp shaft 3. In FIG. 17, the secondary clamping means is actuated by advancing the secondary clamp shaft 4 while the top clamp 2 is still in a clamping position. This action causes bone fragment 90 to be further clamped between spike tip 40 (FIG. 7) and bottom clamping surface 11. Recess 24 (FIG. 5) provides clearance within the body of top clamp 2 for secondary clamp shaft 4. Once the secondary clamp shaft 4 has fully secured bone fragment 90, the primary clamping means is released by retracting the top clamp 2 by turning primary clamp shaft 3. Now the top surface of the bone, or the surface most accessible through the surgical incision, is exposed so that a bone plate or template can be applied.

Figure 18:
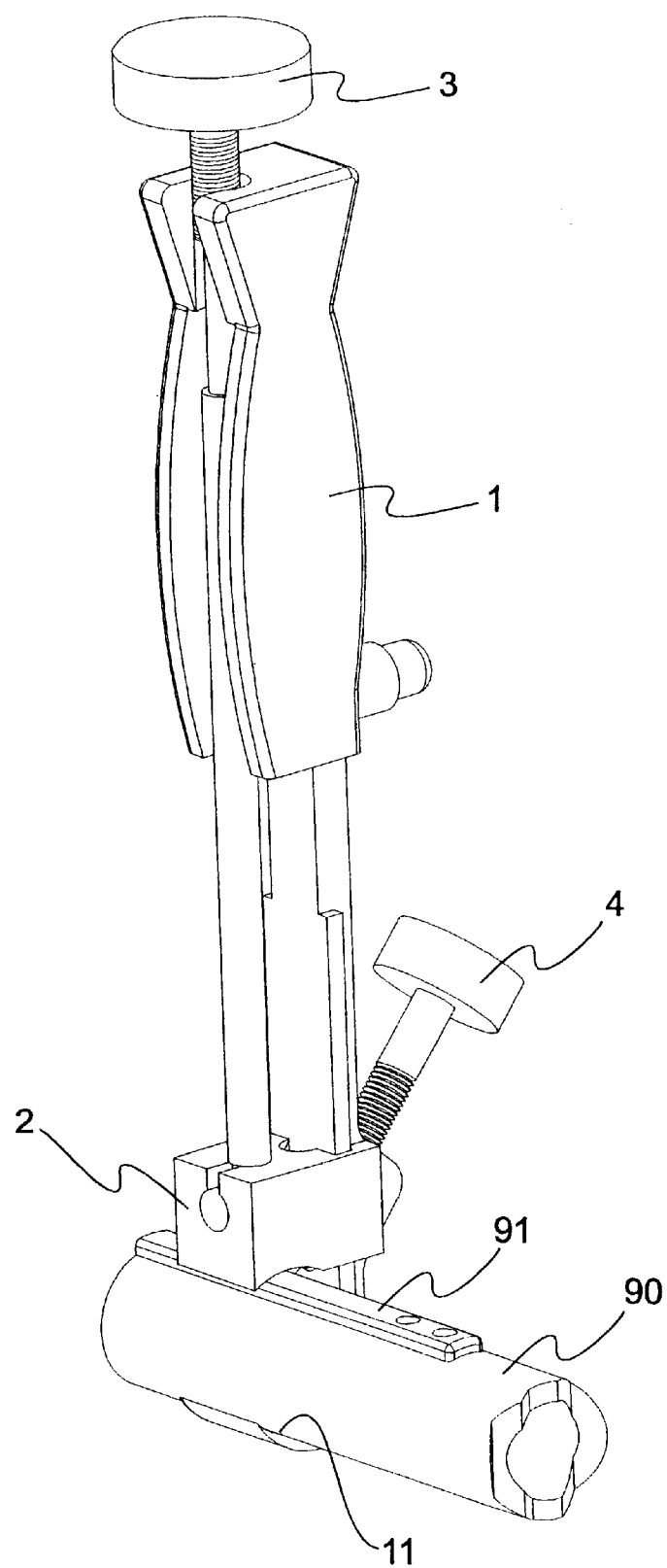
FIG. 18 is a perspective view of the bone clamp holding a bone fragment and a bone plate with the primary clamping means.

Once a bone plate is properly positioned, the bone plate can be clamped to the bone by the primary clamping means. This is illustrated in FIG. 18, where bone plate 91 is held against bone fragment 90 by the clamping force exerted between top clamp 2 and bottom clamp surface 11. This allows the surgical team to maintain accurate positioning of the bone plate 91 while they install bone screws to fix the bone plate 91 to bone fragment 90.

Having described preferred embodiments of the invention with reference to the accompanying drawings, it is to be understood that the embodiments shown herein are by way of example, and that various changes and modifications may be effected by one skilled in the art without departing from the scope or spirit of the invention as defined in the following claims.

What is claimed is:

1. A bone clamp assembly for gripping a single piece of bone, said bone clamp assembly comprising:
    a first clamp for gripping the single piece of bone, said first clamp comprising a first bone contact surface and a second bone contact surface, wherein at least one of the first clamp's first bone contact surface and second bone contact surface is movable towards and away from the other of the first clamp's first bone contact surface and second bone contact surface along a first axis, whereby said first clamp may apply a first gripping force to the single piece of bone; and
    a second clamp for gripping the single piece of bone, said second clamp comprising a first bone contact surface and a second bone contact surface, wherein at least one of the second clamp's first bone contact surface and second bone contact surface is movable towards and away from the other of the second clamp's first bone contact surface and second bone contact surface along a second axis, whereby said second clamp may apply a second gripping force to the single piece of bone;
    with said first clamping force and said second clamping force being applied to the single piece of bone in close proximity to one another so as to effectively act on the same region of the single piece of bone.

2. The bone clamp assembly of claim 1 wherein the first clamp's first bone contact surface is movable towards and away from the first clamp's second bone contact surface, and the second clamp's first bone contact surface is movable towards and away from the second clamp's second bone contact surface.

3. The bone clamp assembly of claim 2 wherein the first clamp's first bone contact surface has a greater surface area than the second clamp's first bone contact surface.

4. The bone clamp assembly of claim 2 wherein the same element forms the first clamp's second bone contact surface and the second clamp's second bone contact surface.

5. The bone clamp assembly of claim 1 wherein said first axis is not parallel to said second axis.

6. The bone clamp assembly of claim 5 wherein said first axis intersects said second axis.

7. A bone setting apparatus comprising a first bone clamp assembly for gripping a first piece of bone, a second bone clamp assembly for gripping a second piece of bone, and a connection apparatus for connecting said first bone clamp assembly to said second bone clamp assembly,
    wherein said first bone clamp assembly comprises:
        a first clamp for gripping the first piece of bone, said first clamp comprising a first bone contact surface and a second bone contact surface, wherein at least one of the first clamp's first bone contact surface and second bone contact surface is movable towards and away from the other of the first clamp's first bone contact surface and second bone contact surface along a first axis, whereby said first clamp may apply a first gripping force to the first piece of bone; and
        a second clamp for gripping the first piece of bone, said second clamp comprising a first bone contact surface and a second bone contact surface, wherein at least one of the second clamp's first bone contact surface and second bone contact surface is movable towards and away from the other of the second clamp's first bone contact surface and second bone contact surface along a second axis, whereby said second clamp may apply a second gripping force to the first piece of bone;
    with said first clamping force and said second clamping force being applied to the first piece of bone in close proximity to one another so as to effectively act on the same region of the first piece of bone; and
    further wherein said second bone clamp assembly comprises:
        a third clamp for gripping the second piece of bone, said third clamp comprising a first bone contact surface and a second bone contact surface, wherein at least one of the third clamp's first bone contact surface and second bone contact surface is movable towards and away from the other of the third clamp's first bone contact surface and second bone contact surface along a third axis, whereby said third clamp may apply a third gripping force to the second piece of bone; and
        a fourth clamp for gripping the second piece of bone, said fourth clamp comprising a first bone contact surface and a second bone contact surface, wherein at least one of the fourth clamp's first bone contact surface and second bone contact surface is movable towards and away from the other of the second clamp's first bone contact surface and second bone contact surface along a fourth axis, whereby said fourth clamp may apply a fourth gripping force to the second piece of bone;
    with said third clamping force and said fourth clamping force being applied to the second piece of bone in close proximity to one another so as to effectively act on the same region of the second piece of bone.

8. The bone setting apparatus of claim 7 wherein said connection apparatus comprises a rod and first and second lockable joints, and wherein said rod is attached to said first bone clamp assembly by said first lockable joint and said rod is attached to said second bone clamp assembly by said second lockable joint.

9. The bone setting apparatus of claim 7 wherein said connection apparatus comprises two rods, and wherein said first rod is attached to said first bone clamp assembly by a first lockable ball and socket joint, wherein said second rod is attached to said second bone clamp assembly by a second lockable ball and socket joint, and further wherein said first and second rods are interconnected by a lockable telescoping joint.

10. The bone setting apparatus of claim 7 wherein the first clamp's first bone contact surface is movable toward and away from the first clamp's second bone contact surface, and the second clamp's first bone contact surface is movable toward and away from the second clamp's second bone contact surface.

11. The bone setting apparatus of claim 7 wherein wherein the first clamp's first bone contact surface has a greater surface area than the second clamp's first bone contact surface, and further wherein the third clamp's first bone contact surface has a greater surface area than the fourth clamp's first bone contact surface.

12. The bone setting apparatus of claim 7 wherein said first axis is not parallel to said second axis, and further wherein the third axis is not parallel to said fourth axis.

13. The bone setting apparatus of claim 7 wherein the same element forms the first clamp's second bone contact surface and the second clamp's second bone contact surface, and further wherein a different element forms the third clamp's second bone contact surface and the fourth clamp's second bone contact surface.

14. The bone setting apparatus of claim 7 wherein said first axis intersects said second axis, and further wherein said third axis intersects said fourth axis.

15. The bone setting apparatus of claim 7 wherein said first and third clamps provide adequate gripping forces for urging the first and second bone fragments into proper alignment, and further wherein said second arid fourth clamps provide adequate gripping forces for holding said proper alignment and further provide adequate clearance for application of a bone prosthesis to the first and second pieces of bone.

16. A bone setting apparatus comprising first and second bone clamp assemblies and a connection apparatus for connecting said first bone clamp assembly to said second bone clamp assembly, wherein said connection apparatus comprises a rod, a first lockable joint for connecting said first bone clamp assembly to said rod, wherein said first lockable joint can selectively provide three degrees of motion between said first bone clamp assembly and said rod, and a second lockable joint for connecting said second bone clamp assembly to said rod, wherein said second lockable joint can selectively provide three degrees of freedom between said second bone clamp assembly and said rod.

17. A method for setting first and second pieces of bone relative to one another, said method comprising the steps of:

providing a first bone clamp assembly comprising first, second and third surfaces, and providing a second bone clamp assembly comprising fourth, fifth and sixth surfaces, and a connector connecting said first bone clamp assembly to said second bone clamp assembly;

moving said first surface towards the second surface so as to grip the first piece of bone therebetween, and moving the fourth surface towards the fifth surface so as to grip the second piece of bone therebetween, whereby to urge the first and second pieces of bone into proper alignment;

moving the third surface toward the second surface so as to grip the first piece of bone therebetween, and moving the sixth surface toward the fifth surface so as to grip the second piece of bone therebetween;

moving the first surface away from the second surface, and moving the fourth surface away from the fifth surface;

securing a prosthesis to the first and second pieces of bone; and moving the third surface away from the second surface, whereby to release first bone clamp assembly from the first piece of bone, and moving the sixth surface away from the fifth surface, whereby to release the second bone clamp assembly from the second piece of bone.

* * * * *